(12) United States Patent
Deaton

(10) Patent No.: US 7,005,522 B2
(45) Date of Patent: *Feb. 28, 2006

(54) SYNTHESIS OF ORGANOMETALLIC CYCLOMETALLATED TRANSITION METAL COMPLEXES

(75) Inventor: Joseph C. Deaton, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/879,657

(22) Filed: Jun. 29, 2004

(65) Prior Publication Data

US 2005/0288507 A1    Dec. 29, 2005

(51) Int. Cl.
*C07F 15/00* (2006.01)
*H05B 33/14* (2006.01)

(52) U.S. Cl. .................. 546/10; 548/108; 556/137; 428/690

(58) Field of Classification Search ............... 546/10; 548/108; 556/137; 428/690

See application file for complete search history.

(56) References Cited

U.S. PATENT DOCUMENTS

2002/0190250 A1    12/2002    Grushin et al ............... 257/40

OTHER PUBLICATIONS

J. C. Deaton, et al., "Synthesis For Organometallic Cyclometallated Transition Metal Complexes", U.S. Appl. No. 10/729,263, (D-87223) filed Dec. 5, 2003.

B. Schmid, et al., "Synthesis and Characterizations of Cyclometalated Iridium (III) Solvento Complexes", Inorg. Chem., vol. 33, No. 1, (1994), pp, 9-14.

*Primary Examiner*—Porfirio Nazario-Gonzalez
(74) *Attorney, Agent, or Firm*—Arthur E. Kluegel

(57) ABSTRACT

A process for forming a tris-cyclometallated iridium or rhodium complex comprises reacting in the presence of a solvent:
a) a bis-cyclometallated complex comprising an Ir (III) or Rh (III) metal, two bidentate ligands, two monodentate ligands and a counterion, and
b) a heterocyclic compound capable of forming an organometallic cyclometallated complex.

28 Claims, No Drawings

SYNTHESIS OF ORGANOMETALLIC CYCLOMETALLATED TRANSITION METAL COMPLEXES

FIELD OF THE INVENTION

This invention relates to the field of organic synthesis and to a process for forming tris-cyclometallated organometallic complexes of the metals Ir(III) or Rh (III) from an intermediate salt complex.

BACKGROUND OF THE INVENTION

Organometallic cyclometallated complexes of transition metals (e.g. rhodium, iridium, platinum) have become useful materials because of their photophysical and photochemical properties. One especially important application of these compounds are as phosphorescent dopants in Organic Light-Emitting Diodes (OLEDs) because of their strong emission from triplet excited states (M. A. Baldo, et al, *Appl. Phys. Letters*, 75, 4 (1999)). An important class of phosphorescent cyclometallated complexes contain ligands that are at least bidentate wherein one coordination site of the ligand to the metal is through an N atom that is doubly bonded to C or another N atom, usually as part of a heterocyclic ring, and wherein another coordination site of the ligand to the metal is through a C atom. As used herein, the term "organometallic cyclometallated complex" means that at least one of the coordination sites forming the cyclic unit binding the metal atom by at least one ligand must be a metal-carbon bond. The metal-carbon bond is formed in place of a hydrogen-carbon bond of the free ligand before it is complexed. The carbon atom forming the metal carbon bond is usually also doubly bonded to another carbon as in, for example, a phenyl ring or a thienyl ring or furanyl ring. Further the carbon atom forming the metal-carbon bond also is preferably positioned so as to form a five- or six-membered metallacycle including the coordinated N atom of the ligand. A tris-cyclometallated complex has three such ligands. Some examples of iridium(III) organometallic cyclometallated complexes are shown below.

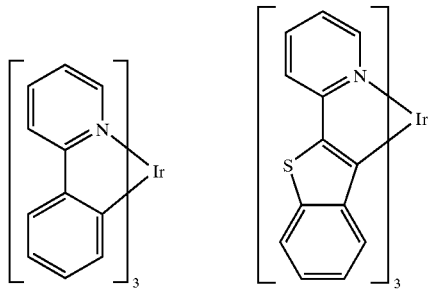

Further, there are two isomers, facial and meridional (fac and mer), possible for such complexes having three identical but unsymmetrical bidentate ligands as illustrated below. The facial isomers are typically more desirable in OLED applications because they usually have higher quantum yields.

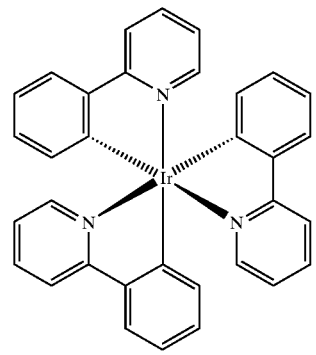

Fac

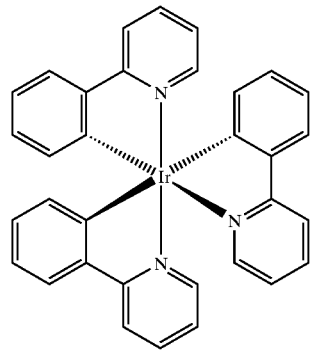

Mer

It is also possible that the organometallic cyclometallating ligands are not all the same. Further, the organometallic cyclometallated complex must have at least one cyclometallating ligand forming a metal-carbon bond, but may have additional types of ligands not forming metal-carbon bonds. A common type of the latter would be complexes of the form $L_2MX$ as described in WO 02/15645. Here L is a cyclometallating ligand forming metal-carbon and metal-nitrogen bonds, while X is another monoanionic bidentate ligand that does not form metal carbon bonds, such as acetylacetonate.

The usefulness and importance of organometallic cyclometallated complexes of second- and third-row transition metals have necessitated synthetic methods for preparing them more efficiently. Chassot et al., *Inorg. Chem.*, 23, 4249–4253, (1984) have used lithiated ligands with platinum compounds that include leaving groups to form cyclometallated complexes of the ligands with platinum. Jolliet et al., *Inorg. Chem.*, 35, 4883–4888, (1996) also used lithiated ligands to form cyclometallated complexes of the ligands with platinum or palladium, and Lamansky and Thompson, in WO 00/57676, used the same procedure for cyclometallated platinum complexes. These procedures suffer from low yields, as well as the relative instability of and difficulty in handling lithiated organic materials.

Organometallic cyclometallated complexes may also be formed from direct reaction of the cyclometallating ligand, wherein the carbon-hydrogen is activated and replaced by the carbon-metal bond. For example, fac-tris(2-phenylpyridinato-N,$C^{2'}$)iridium(III), or Ir(ppy)$_3$, was made by reaction of 2-phenylpyridine and tris(acetylacetonate)iridium(Ir(acac)$_3$) in glycerol solvent by K. Dedian et al, *Inorg. Chem.*, 30, 1685 (1991). Stössel and coworkers (WO 02060910) further optimized and improved this reaction, but still using the expensive Ir(acac)$_3$ starting material. By reacting less expensive halide complexes of IR(III) such as iridium(III) chloride hydrate with 2-phenylpyridine in a solvent comprising a 3:1 mixture of 2-ethoxy-ethanol and water, Nonoyama obtained dimeric organometallic cyclometallated complexes such as tertakis(2-phenylpyridinato-N,$C^{2'}$-) (di- μ-chloro)di-iridium(III). (Note: Ir(ppy)₃ was later extracted as a side product in 10% yield from this reaction mixture, K. A. King, et al., *J. Am. Chem. Soc.*, 107, 1431 (1985).) M. G. Colombo, et al *Inorg Chem.*, 33, 545 (1994), further reacted the above-cited di-iridium complex with a silver salt in neat 2-phenylpyridine to obtain Ir(ppy)₃ in 75% yield. Grushin et al., U.S. 2002/0190250, used this process to make additional tris-cyclometalated complexes of Ir(III) having fluorine-substitutions on phenylpyridine and phenylquinoline cyclometallating ligands. But this process requires a large excess of a ligand since it is employed as the solvent, thereby either consuming valuable material or necessitating a process to recover excess ligand.

Lamasky et al., *Inorg. Chem.*, 40, 1704–1711, (2001) demonstrated yet another process for making tris-cyclometallated iridium complexes. First, a mixed ligand complex, bis(7,8-benzoquinolinato-N,C³')iridium(III)(acetylacetonate), was made from tetrakis(7,8-benzoquinolinato-N,C³')(di-μ-chloro)di-iridium(III). Then the bis(7,8-benzoquinolinato-N,C³')iridium(III)(acetylacetonate) was reacted with additional 7,8-benzoquinoline in refluxing glycerol to produce a mixture of isomers of the tris-cyclometallated complex, tris(7,8-benzoquinolinato-N,C³')iridium(III). Kamatani et al., U.S. 2003/0068526, have also employed this reaction type for additional cyclometallated iridium complexes. But this process often yields less-desirable meridional isomers or mixtures of the facial and meridonal isomers of the tris-cyclometallated complexes. This process also requires very long reaction times at elevated temperatures in the case of many other desired ligands to completely replace the acetylacetonate or similar anionic bidentate ligand with the desired organometallic cyclometallating ligand. Tamayo et al., *J. Am. Chem. Soc.*, 125, 7377–7387 (2003), have shown that reaction of dimeric organometallic cyclometallated complexes such as tetrakis(2-phenyl-pyridinato-N, C²'-)(di-μ-chloro)di-iridium(III) with sodium carbonate and additional cyclometallating ligand in glycerol can lead to formation of meridional isomers in many cases, while further reaction at higher temperatures results in formation of mostly facial isomer. However, this procedure is inconvenient for facial isomers as it necessitates finding exact conditions for the reaction of each ligand.

Copending U.S. Ser. No. 10/729,263 describes a process for forming organometallic cyclometallated complexes of Ir(III) comprising the step of reacting a halide-containing complex of the metal with a silver salt and a heterocyclic organic ligand compound capable of forming an organometallic cyclometallated complex and in a solvent comprising an organic diol. However, this process fails or works poorly in many cases of desirable ligands. One of the possible reason for this process not being generally applicable to a wide variety of possible cyclometallating ligands is that the solubility of the intermediate complexes may be too low in these solvents.

B. Schmid, F. Garces, and R. Watts, *Inorg. Chem.*, 33, 9 (1994), describe the preparation of solvento complexes of iridium that additionally comprise cyclometallating ligands. However these materials comprise cationic complexes that are not volatile enough for vapor deposition and therefore are not as useful as tris-cyclometallated complexes for EL applications.

Despite the large number of investigations into the synthetic methodology for cyclometallated organometallic complexes, there remains a need for methods that may provide better yields, higher purity, and control of desired isomers.

SUMMARY OF THE INVENTION

The invention provides a process for forming a tris-cyclometallated iridium or rhodium complex comprises reacting in the presence of a solvent:
a) a bis-cyclometallated complex comprising an Ir (III) or Rh (III) metal, two bidentate ligands, two monodentate ligands and a counterion, and
b) a heterocyclic compound capable of forming an organometallic cyclometallated complex. Such a process may improve the yields, purity and/or desired isomer control.

DETAILED DESCRIPTION OF THE INVENTION

The invention is summarized above. The process involves forming a tris-cyclometallated organometallic iridium or rhodium complex from a mononuclear, bis-cyclometalled organometallic complex that additionally comprises two monodentate ligands and a counterion. In one desirable embodiment the organometallic complexes are iridium complexes. In one aspect of the invention, the bis-cyclometallated complex is cationic and the counterion is anionic. In another desirable embodiment, the bis-cyclometallated complex is anionic and the counterion is cationic.

In one embodiment the bis-cyclometallated complex is represented by Formula (1).

$$[(L^1)_2M(L^2)_2]X \qquad (1)$$

In Formula (1), M represents Ir or Rh; in one desirable embodiment M represents Ir. In Formula (1), X represents a counterion to balance the charge of the complex. Thus if the complex is cationic, then the counterion, X, represents an anionic counterion, for example, a tetrafluoroborate or hexafluorophosphonate ion. If the complex is anionic then the counterionic, X, represents a cationic counterion, for example, a sodium, potassium or tetrabutylammonium ion. Each $L^1$ in Formula (1), represents an independently selected bidentate cyclometallating ligand and each $L^1$ may be the same or different. In one embodiment, $L^1$ represents the same ligand in each case. As described previously and as used herein for forming organometallic complexes, a bidentate cyclometallating ligand is a ligand wherein one coordination site of the ligand to the metal is through an N atom that is doubly bonded to C or another N atom, usually as part of a heterocyclic ring, and wherein another coordination site of the ligand to the metal is through a C atom. Illustrative examples of bidentate cyclometallating ligands are listed below.

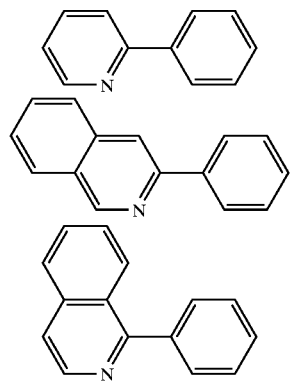

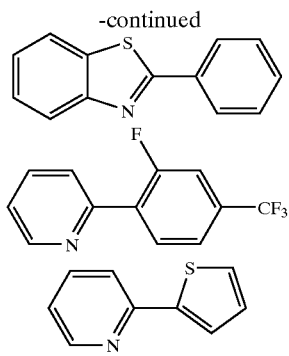

Each $L^2$ in Formula (1), represents an independently selected monodentate ligand, which may be the same or different. In one embodiment the monodentate ligands are the same. Monodentate ligands form only one bond to the metal.

In one desirable embodiment the monodentate ligand is not charged. In this case the complex is cationic and the counterion, X, represents an anion. For example, suitable neutral monodentate ligands include nitriles, such as acetonitrile and propionitrile, sulfoxides, such as dimethylsulfoxide, amides such as dimethylformamide, ethers, such as tetrahydrofuran, water, ammonia, amines, piperidine, pyridine, and pyrazine.

One embodiment includes monodentate ligands which are sulfur-donor ligands such as thioethers, thiols, thioureas, or phosphoruos or arsenic donor ligands such as triaryl or trialkyl phosphines.

In one especially desirable embodiment the neutral monodentate ligand is a nitrile. A particularly suitable ligand is acetonitrile.

In one embodiment, the two neutral monodentate ligands may be joined to form a neutral bidentate ligand. Examples include ethylene diamine, bipyridyl, and phenanthroline. However, in one desirable embodiment the monodentate ligands are not joined because separate monodentate ligands may be more easily displaced from a complex than a bidentate ligand in the succeeding step of the invention process according to the principle of the chelate effect (J. E. Huheey, Inorganic Chemistry, $2^{nd}$ ed., Harper & Row, New York, 1978, p. 481–487).

In another suitable embodiment, the monodentate ligand is anionic. In this case the complex is anionic and the counterion, X, represents a cation. Examples of anionic ligands include hydroxide, alkoxides, phenoxides, thiocyanate, cyanate, and isocyanate.

Illustrative examples of Formula (1) compounds are listed below.

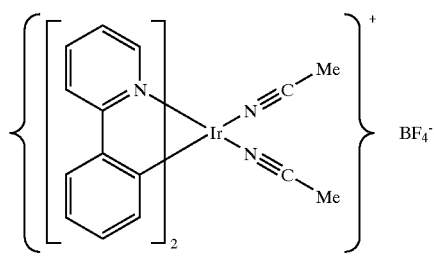

1a

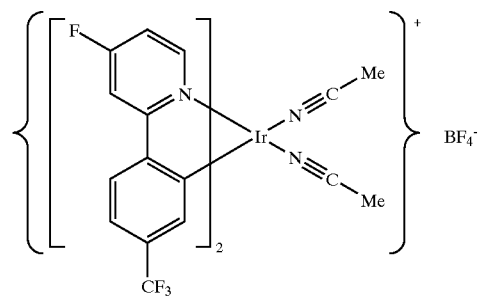

1b

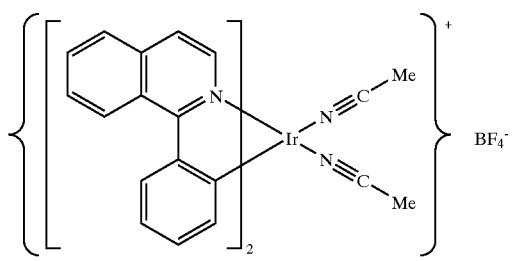

1c

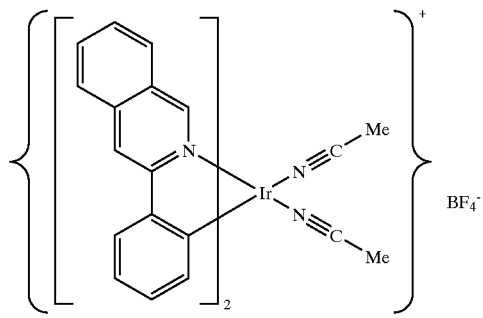

1d

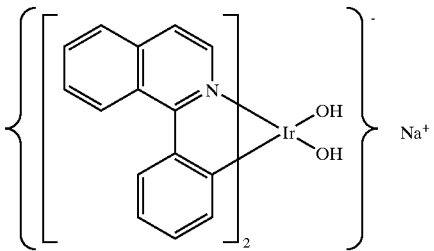

1e

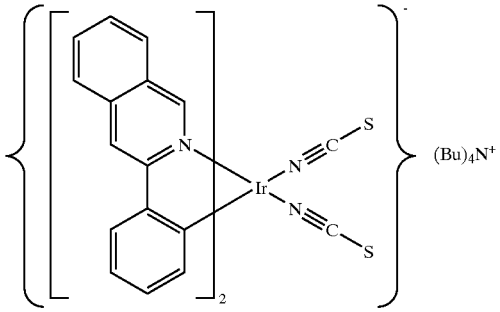

1f

-continued

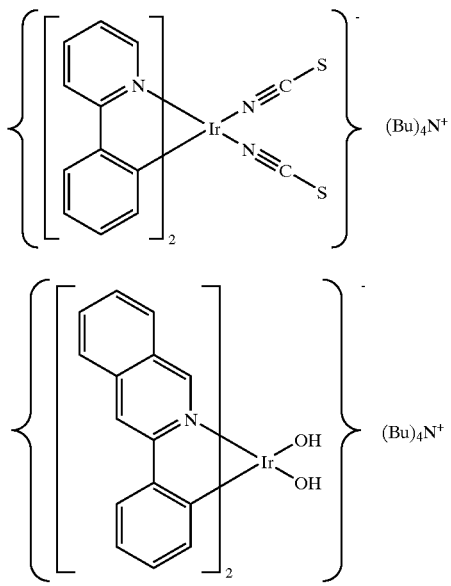

1g

1h

The bis-cyclometallated complexes, such as those represented by Formula (1), can be prepared by reaction of the monodentate ligand with a tetrakis-cyclometallated di-halide di-metal complex, represented by Formula (A), see B. Schmid, F. Garces, and R. Watts, *Inorg. Chem.*, 33, 9 (1994). Bis-cyclometallated complexes represented by Formula (1) wherein the mondentate ligands are joined to form a bidentate ligand can be prepared from the compounds represented by Formula (A) according to the methods in F. O. Garces, K. A. King, and R. J. Watts, *Inorg. Chem.*, 27, 3464 (1988).

$$(L^1)_2M(\mu-X)_2M(L^1)_2 \tag{A}$$

In Formula (A), M and $L^1$ were described previously. Each $\mu-X$ represents a bridging halide, such as Br or Cl. Complexes of Formula (A) may be prepared by literature methods, see for example, Tamayo et al., *J. Am. Chem. Soc.*, 125, 7377–7387 (2003) and references cited therein and previously mentioned U.S. Ser. No. 10/729,263. In the formation of the complexes of Formula (1), a silver salt, such as silver tetrafluoroborate or silver trifluoromethane sulfonate, is often added along with the monodentate ligand to promote displacement of the bridging halide from the complex of formula (A). Further, in the case when a neutral monodentate ligand is desired, it is may be particularly convenient to use that ligand as a solvent for the reaction of a complex of Formula (A) to form a complex of Formula (1), and for such solvent and ligand to be selected from those having a low boiling point that may be easily concentrated or removed by evaporation. For example, a convenient solvent that may also serve as neutral monodentate ligand is acetonitrile. Another convenient solvent that could also serve as ligand would be tetrahydrofuran.

It should be noted that, in some cases, the monodentate ligands in Formula (1) may be displaced or partly displaced, inadvertently or otherwise, by other monodentate ligands, such as water or methanol molecules, as reported in B. Schmid, F. Garces, and R. Watts, *Inorg. Chem.*, 33, 9 (1994), and that use of such resultant compounds or mixtures of compounds are included in the process of the present invention.

The process of the invention to prepare tris-cyclometallated organometallic complexes includes reacting a bis-cyclometallated complex of Formula (1) with a heterocyclic compound capable of forming an organometallic tris-cyclometallated complex. In one embodiment the heterocyclic compound includes a bidentate cyclometallating ligand, as described previously for $L_1$. Suitable examples of bidentate cyclometallating ligands include 2-phenylpyridine group, a 1-phenylisoquinoline group or a 3-phenylisoquinoline group.

Useful solvents for the step of forming the tris cyclometallated complex from complexes of Formula (1) include aliphatic alcohols, glycerol, aliphatic diols, aromatic alcohols and diols, aromatic esters and ethers. In one embodiment the solvent comprises an aliphatic diol or an aromatic ester. Illustrative examples of solvents useful in the invention include 1-propanol, 2-ethoxy ethanol, phenoxyethanol, glycerol, ethylene glycol, 1,2-propanediol, 1,3-propanediol, 1,3-butanediol, and phenyl acetate.

The reaction mixtures may be conveniently heated to the reflux temperature of the solvent, or may be held in a constant temperature bath. A suitable temperature range for the reactions is 70 to 250° C. but more commonly is 140 to 220° C.

The process is carried out for a sufficient length of time to produce substantial amounts of the tris-cyclometallated complex. Suitable reaction times can be determined by monitoring the reaction. For example, by removing aliquots of the reaction mixture periodically and by using thin-layer-chromatography (TLC) or high-performance-liquid chromatography (HPLC) analysis one can determine the amount of reactants present, e.g., unreacted bis-cyclometallated complex, and one can determine the amount of product formed. In this manner the progress of the reaction can be monitored. Typically the reaction times are 1 to 24 h, but may be shorter or longer.

Suitably the tris-cyclometallated product can be isolated and purified if necessary. Purification can be done by well-known methods such as sublimation, crystallization or column chromatography.

In one suitable embodiment, the tris-cyclometallated product is represented by Formula (2).

$$M(L^1)(L^2)(L^3) \tag{2}$$

In Formula (2), M represents Ir or Rh and $L^1$, $L^2$, and $L^3$ represent bidentate cyclometallating ligands which may be the same or different. In one desirable embodiment the ligands are the same. Suitably, $L^1$ and $L^2$ may be the same and $L^3$ may be different. In another suitable embodiment the bidentate cyclometallating ligands comprise a 2-phenylpyridine group, a 1-phenylisoquinoline group or a 3-phenylisoquinoline group. Illustrative examples of tris-cyclometallated compounds of Formula (2) are listed below.

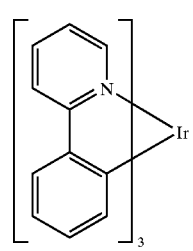

2a

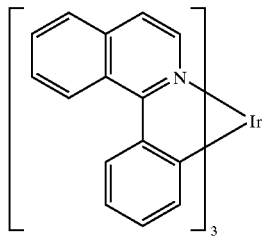
2b
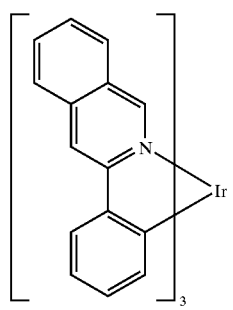
2c
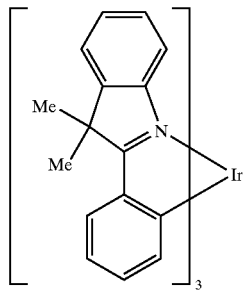
2d
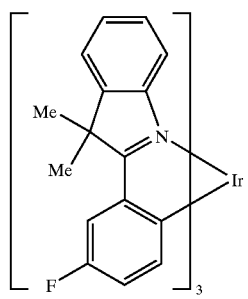
2e
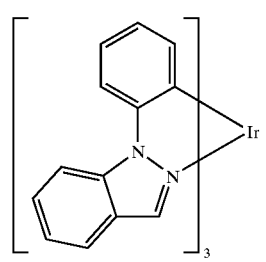
2f
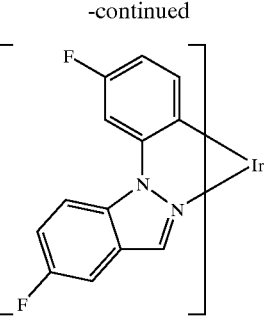
2g
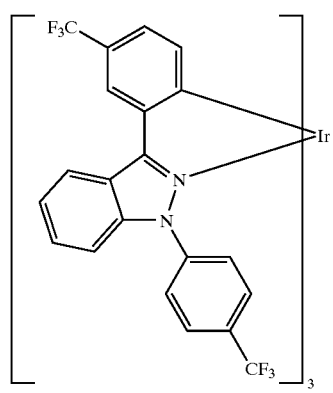
2h
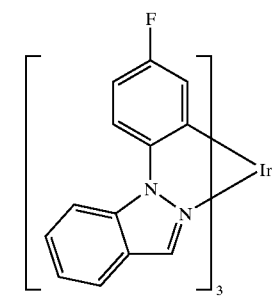
2i
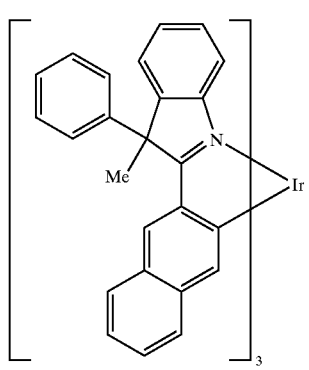
2j
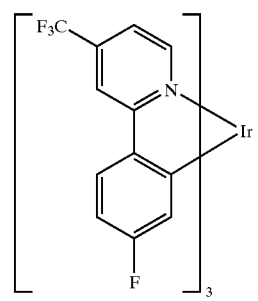
2k -continued

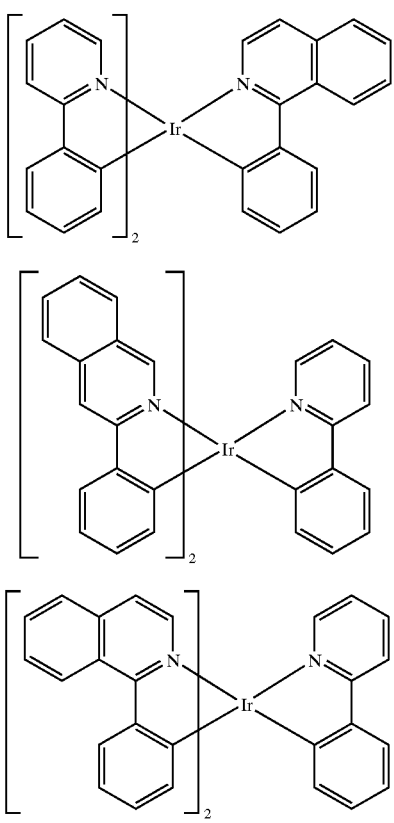

Embodiments of the invention may provide convenient methods of synthesis, employ relatively inexpensive starting materials and solvents, and be applicable to a wide range of cyclometallating ligands. Embodiments may also provide higher yields of tris-cyclometallated complexes having fewer impurities.

The invention and its advantages can be better appreciated by the following examples.

EXAMPLE 1

Preparation of
fac-tris(2-phenylpyridinato-N,$C^{2'}$)iridium(III)

$K_3IrBr_6$(7.75 g, 9.82 mmol) was placed in a 200 mL flask with 75 mL of 2-ethoxyethanol, 25 mL water, and 2-phenylpyridine (4.2 mL). The mixture was freeze-thaw degassed, and then refluxed for 4 h under nitrogen atmosphere during which time a yellow-orange precipitate appeared. After cooling, the precipitate was collected by filtration, washed with 1 N HBr(aq), then water, and dried to yield yellow tetrakis(2-phenylpyridinato-N,$C^{2'}$)($\mu$-dibromo)diiridium(III) (5.02 g, 88% yield based on iridium).

Tetrakis(2-phenylpyridinato-N,$C^{2'}$)($\mu$-dibromo)diiridium (III) (0.68 g, 0.585 mmol) and silver tetrafluoroborate (0.25 g, were placed in a 100-mL round-bottomed flask with 30 mL of acetonitrile and the mixture was freeze-thaw degassed, and then refluxed for 3 h under nitrogen atmosphere. After cooling, the yellow solution was filtered to remove white insoluble material and the solvent was removed under vacuum. The resulting solid was crystallized from methanol, collected, and dried to afford 0.60 g of product. Analysis by $H^1$ NMR spectroscopy and mass spectrometry confirmed that this material was bis(acetonitrile)bis[(2-phenylpyridinato-N,$C^{2'}$)]iridium(III) tetrafluoroborate.

Bis(acetonitrile)bis[(2-phenylpyridinato-N,$C^{2'}$)]iridium (III)tetrafluoroborate (0.56 g, 0.84 mmol) was placed in a 100-mL round-bottomed flask with 30 mL of propanediol and 2-phenylpyridine (0.30 mL) and the mixture was freeze-thaw degassed, and then refluxed for 4 h under nitrogen atmosphere during which time a yellow precipitate appeared. After cooling, the precipitate was collected by filtration, washed with ethanol and dried to afford 0.52 g of product (94.9% yield). Analysis by high-performance-liquid-chromatography and mass spectroscopy confirmed that this material was fac-tris(2-phenylpyridinato-N,$C^{2'}$)iridium (III) of high purity.

EXAMPLE 2

Preparation of
fac-tris(3-phenylquinolinato-N,$C^{2'}$)iridium(III)

Tetrakis(3-phenylisoquinolinato-N,$C^{2'}$)($\mu$-dibromo)diiridium(III) (0.72 g, 0.526 mmol) and silver tetrafluoroborate (0.23 g.) were placed in a 100 mL round-bottomed flask with 30 mL of acetonitrile and the mixture was freeze-thaw degassed, and then refluxed for 2 h under nitrogen atmosphere. After cooling, the yellow solution was filtered to remove white insoluble material and the solvent was removed under vacuum. The resulting solid was dried to afford 0.76 g of yellow product. Analysis by mass spectrometry confirmed that this material was bis(acetonitrile)bis[(3-phenylisoquinolinato-N,$C^{2'}$)]iridium(III) tetrafluoroborate.

Bis(acetonitrile)bis[(3-phenylisoquinolinato-N,$C^{2'}$)]iridium(III)tetrafluoroborate (0.636 g, 0.83 mmol) and 3-phenylisoquinoline (0.42 g, were placed in a 100-mL round-bottomed flask with 35 mL of 1,2-propanediol and the mixture was freeze-thaw degassed, and then refluxed for 4 h under nitrogen atmosphere during which time an orange precipitate appeared. After cooling, the precipitate was collected by filtration, washed with ethanol and dried to afford 0.63 g of product (95% yield). Analysis by high-performance-liquid-chromatography and mass spectroscopy confirmed that this material was fac-tris(3-phenylisoquinolinato-N,$C^{2'}$)iridium(III) of high purity.

EXAMPLE 3

Preparation of
fac-tris(1-phenylisoquinolinato-N,$C^{2'}$)iridium(III)

Tetrakis(1-phenylisoquinoline-N,$C^{2'}$)($\mu$-dibromo)diiridium(III) (2.06 g, 1.51 mmol) and silver tetrafluoroborate (0.648 g, were placed in a 100-mL round-bottomed flask with 35 mL of acetonitrile and the mixture was freeze-thaw degassed, and then refluxed for 3 h under nitrogen atmosphere. After cooling the dark orange solution was filtered through Celite to remove gray insoluble material and the solvent was removed under vacuum until a precipitate formed. Diethyl ether was added to further precipitate the product, which was then collected by filtration and dried to afford 1.870 g of material. A second crop (0.280 g) was obtained by further concentrating the filtrate and adding additional diethyl ether. NMR and mass spectrometry confirmed the product was bis(acetonitrile)bis[(1-phenyliisoquinolinato-N,$C^{2'}$)]iridium(III) tetrafluoroborate The total yield of bis(acetonitrile)bis[(1-phenylisoquinolinato-N,$C^2$)] iridium(III) tetrafluoroborate was 2.15 g (88.2%).

Bis(acetonitrile)bis[(1-phenylisoquinolinato-N,$C^2$)]iridium(III)tetrafluoroborate (1.12 g, 1.455 mmol) and 1-phenylisoquinoline (0.747 g) were placed in a 100-mL round-bottomed flask with 35 mL of 2-ethoxyethanol and the mixture was freeze-thaw degassed and then refluxed for 16 h under nitrogen atmosphere. After cooling, the dark purple precipitate was collected by filtration, washed with methanol and then diethyl ether (approximately 300 mL) and then washed with another portion of methanol (25 mL). The solid was dried to afford 0.977 g (83.4% yield) of product. Analysis by NMR, mass spectrometry, and high-performance-liquid-chromatography confirmed that this material was fac-tris(1-phenyl-isoquinolinato-N,$C^2$)iridium(III) of high purity.

As can be seen from the above examples, the process provides a simple method to prepare tris-cyclometallated metal complexes in high yield and purity. The tris-cyclometallated metal complexes synthesized according to this invention may be incorporated in an EL device. In one embodiment the tris-cyclometallated metal complexes are included in a light-emitting layer of an EL device.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

What is claimed is:

1. A process for forming a tris-cyclometallated iridium or rhodium complex comprising reacting in the presence of a solvent:
   a) a bis-cyclometallated complex comprising an Ir (III) or Rh (III) metal, two bidentate ligands, two monodentate ligands and a counterion, with
   b) a heterocyclic compound capable of forming an organometallic cyclometallated complex.

2. A process according to claim 1 wherein the metal is Ir (III).

3. A process according to claim 1 wherein the bis-cyclometallated complex is cationic and the counterion is anionic.

4. A process according to claim 1 wherein the bis-cyclometallated complex is anionic and the counterion is cationic.

5. A process according to claim 1 wherein at least one bidendate ligand comprises a 2-phenylpyridine group.

6. A process according to claim 1 wherein at least one bidendate ligand comprises a 3-phenylisoquinoline group.

7. A process according to claim 1 wherein at least one bidendate ligand comprises a 1-phenylisoquinoline group.

8. A process according to claim 3 wherein at least one monodentate ligand is an aliphatic nitrile.

9. A process according to claim 3 wherein at least one monodentate ligand is acetonitrile.

10. A process according to claim 3 wherein the counter ion comprises fluoride.

11. A process according to claim 3 wherein the counter ion comprises $BF_4^-$ or $PF_6^-$.

12. A process according to claim 4 wherein at least one monodentate ligand is thiocyanate.

13. A process according to claim 1 wherein the heterocyclic compound comprises a 2-phenylpyridine group.

14. A process according to claim 1 wherein the heterocyclic compound comprise a 3-phenylisoquinoline group.

15. A process according to claim 1 wherein the heterocyclic compound comprise a 1-phenylisoquinoline group.

16. A process according to claim 1 wherein the solvent is an alcohol.

17. A process according to claim 1 wherein the solvent is a diol.

18. A process according to claim 1 wherein the solvent is an organic ester.

19. A process according to claim 1 wherein the bis-cyclometallated complex is represented by Formula (1):

$$[(L^1)_2M(L^2)_2]X \quad (1)$$

wherein:
   M represents Ir or Rh;
   X represents a counterion;
   each $L^1$ represents an independently selected bidentate cyclometallating ligand; and
   each $L^2$ represents an independently selected monodentate ligand.

20. A process according to claim 19 wherein at least one of $L^1$ represents a phenylpyridine group.

21. A process according to claim 19 wherein at least one of $L^2$ represents an aliphatic nitrile.

22. A process according to claim 19 wherein at least one of $L^2$ represents acetonitrile.

23. A process according to claim 19 wherein at least one of $L^2$ represents thiocyanate.

24. A process according to claim 1 wherein the tris-cyclometalled complex is represented by Formula (2):

$$M(L^1)(L^2)(L^3) \quad (2)$$

wherein:
   M represents Ir or Rh; and
   $L^1$, $L^2$, and $L^3$, represent independently selected bidentate cyclometallating ligands.

25. A process according to claim 24 wherein $L^1$, $L^2$, and $L^3$ represent the same bidentate ligand.

26. A process according to claim 24 wherein $L^1$, $L^2$, and $L^3$ represent independently selected phenylpyridine groups.

27. A process according to claim 24 wherein at least one of $L^1$, $L^2$, and $L^3$ represents a 1-phenylisoquinoline group.

28. A process according to claim 24 wherein at least one of $L^1$, $L^2$, and $L^3$ represents a 3-phenylisoquinoline group.

* * * * *